United States Patent [19]
Gruber

[11] Patent Number: 4,570,487
[45] Date of Patent: Feb. 18, 1986

[54] MULTIBEAM SATELLITE-PULSE OBSERVATION TECHNIQUE FOR CHARACTERIZING CRACKS IN BIMETALLIC COARSE-GRAINED COMPONENT

[75] Inventor: George J. Gruber, San Antonio, Tex.

[73] Assignee: Southwest Research Institute, San Antonio, Tex.

[21] Appl. No.: 588,898

[22] Filed: Mar. 12, 1984

Related U.S. Application Data

[63] Continuation-in-part of Ser. No. 268,145, May 28, 1981, Pat. No. 4,435,984, which is a continuation-in-part of Ser. No. 142,216, Apr. 21, 1980, Pat. No. 4,299,128.

[51] Int. Cl.$^4$ .............................................. G01N 29/04
[52] U.S. Cl. ........................................ 73/624; 73/628
[58] Field of Search ................ 73/624, 620, 625, 627, 73/628, 641, 1 DV

[56] References Cited

U.S. PATENT DOCUMENTS

| | | | |
|---|---|---|---|
| 3,592,052 | 7/1971 | Di Giacomo | 73/620 |
| 3,683,680 | 8/1972 | Johnson et al. | 73/628 |
| 3,972,228 | 8/1976 | Mansson | 73/609 |
| 4,137,779 | 2/1979 | Wustenberg et al. | 73/627 |

FOREIGN PATENT DOCUMENTS

| | | |
|---|---|---|
| 1448471 | 9/1976 | United Kingdom . |
| 2043899 | 10/1980 | United Kingdom . |

OTHER PUBLICATIONS

M. G. Silk et al., "Ultrasonic Time-Domain Measurements of the Depth of Crack Like Defects in Ferritic and Austenitic Steels", *Proceedings of Specialist Meeting on Ultrasonic Inspection of Reactor Components*, pp. 1-17, Sep. 1976.
B. Trumpff et al., "Contribution Improving Ultra. Testing of Thick Bimetallic Welds", *CSNI Specialist Meeting*, pp. 25-54, May 1980.
X. Edelmann, "Practical Applications of Ultra. Testing of Aus. Weld Joints", *Materials Evaluation*, pp. 47-51, Sep. 1979.
N. V. Vinogradow et al., "Dissipation of Ultra. Osc. at Boundary Layers of Bimetal Made by Explosive Welding", *Soviet Journal NDT*, 12, pp. 647-651, Nov. 1976.
R. J. Hudgell et al., "Ultrasonic Longitudinal-Wave Exam of Aus. Welds", *British Jour. of NDT*, 22, pp. 78-85, Mar. 1980.
D. S. Kupperman et al., "Effects of Microstructure on Ultra Exam of Stainless Steel," *CSNI Specialist Meeting*, Sep. 1976.
D. S. Kupperman et al., "Effect of Shearwave Polarization on Defect Detection in Stainless Steel Weld," *Ultrasonics*, pp. 21-27, Jan. 1978.
P. Caussin et al., "Factors Affecting Ultra. Exam of Aus. Components", *CSNI Specialist Meeting*, pp. 421-439, May 1980.
G. J. Gruber et al., "Detection of Surface Cracks in Bimetallic Structures—A Reliability Eval. of Five Ultra. Tech.," *Proceedings of 11th Nuclear Power Ed. Seminar*, pp. 1-35, Apr. 1981.
*Proceedings of Committee on Safety of Nuclear Install. Specialist Meeting Reliability of Ultra Insp of Austenitic Mat. and Comp.*, May 1980.

*Primary Examiner*—Stephen A. Kreitman
*Attorney, Agent, or Firm*—Gunn, Lee & Jackson

[57] ABSTRACT

Ultrasonic testing methods and units for characterizing planar flaws in hard-to-inspect materials such as welded and cladded pipes containing intergranular stress corrosion cracks. The invention characterizes flaws with pitch-catch transducers positioned front to back on a single module. One module uses a bimodal transducer to transmit longitudinal and shear waves to produce, through surface wave mode conversion, reflection and diffraction, a triplet of associated longitudinal and shear wave signals received by another bimodal transducer. Other modules use pitch-catch transducers to produce a doublet of associated shear wave signals from diffraction of an incident longitudinal and/or shear waves at the upper and lower extremities of underclad fatigue cracks and buried cracks. The signals are enchanced by multiple one sided cross focusing on preselected target areas in the test specimen and are cognizable by pattern recognition. Flaw characterization results from the created linear relationship between signal separation and crack depth.

40 Claims, 22 Drawing Figures

MODULE SLIC-40

SLIC-50 MODULE POSITION 3

SLIC-50 MODULE POSITION 4

SLIC-50 MODULE POSITION 5

MODULE SSIC-50 POSITIONS

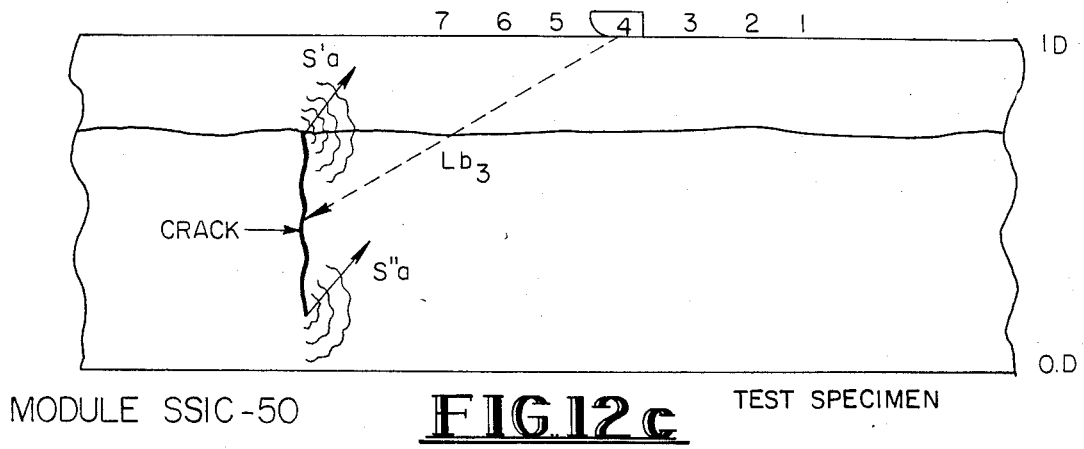
MODULE SSIC-50    FIG.12c    TEST SPECIMEN
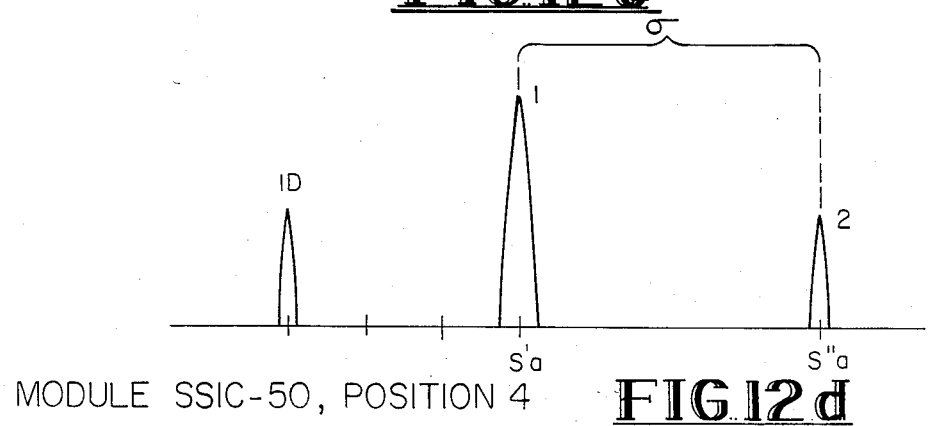
MODULE SSIC-50, POSITION 4    FIG.12d
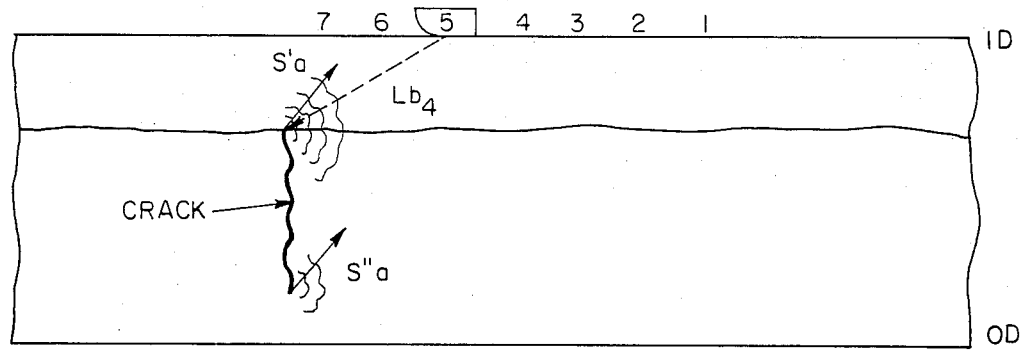
MODULE SSIC-50    FIG.12e    TEST SPECIMEN
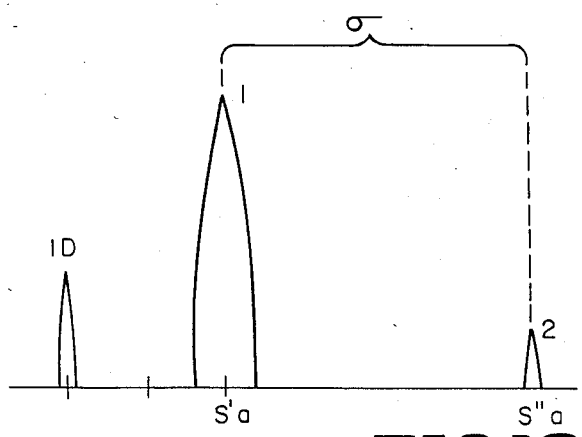
MODULE SSIC-50, POSITION 5    FIG.12f

MULTIBEAM SATELLITE-PULSE OBSERVATION TECHNIQUE FOR CHARACTERIZING CRACKS IN BIMETALLIC COARSE-GRAINED COMPONENT

CROSS REFERENCES TO RELATED APPLICATION

This application in a continuation-in-part application of U.S. Pat. No. 4,435,984 filed May 28, 1981, by the same inventor for Ultrasonic Multiple-Beam Technique For Detecting Cracks In Bimetalic Or Coarse-Grained Materials and is further a continuation-in-part application of U.S. Pat. No. 4,299,128 filed Apr. 21, 1980, Ser. No. 142,216, by the same inventor for Ultrasonic Satellite-Pulse Technique For Characterizing Defects Of Arbitrary Shape, of which the above U.S. Pat. No. 4,435,984 is a continuation-in-part, which are both incorporated herein for all purposes.

BACKGROUND

Inner and outer surface cladding of pipes and vessels and welding of such components create numerous inspection difficulties which the current nondestructive testing art does not satisfactorily surmount. The problem is not usually a lack of ultrasonic indications but rather the inability of conventional methods to discriminate against the false indications and productively use the true indications. Inner and outer stainless steel cladding defeat many test methods due to the clad-base metal interface creating multiple scatterers, the material inhomogeneity and anisotropy inherent in cladded components, the possibility of buried flaws, etc. Welds produce additional scatterers, interfaces, material inhomogenieties and buried flaws and often join other structures to the surface of the component which limit the inspector's access to either the right side or left side of the flaw and/or to the inside or outside surface of the component. Further, testing for underclad cracks which originate at the clad-base metal interface or near mid-wall in a pressure vessel present additional testing difficulties because these flaws are without a strongly reflective corner as is the case for a surface connected crack.

Unfortunately, these difficulties are often simultaneously present and synergistically combine to create inspection difficulties. Further, the very subjects of the above described inspection difficulties, i.e. welds and cladding are often the very source and location of cracks. These matters are of the greatest commercial importance as many of the difficult-to-inspect components are found in nuclear reactor vessels and coolant piping to nuclear reactor vessels.

These and other test difficulties currently existent in the nondestructive testing art are described in greater detail herein and in the above related applications. The prior art disclosed by the inventor and cited by the examiner in the above related applications is material to the current invention and is expressly incorporated herein.

Other material art includes Silk, M. G., Lidington, B. M., Montgomery, P., and Hammond, C. G., "Ultrasonic Time-Domain Measurements of the Depth of Crack-Like Defects in Ferritic and Austenitic Steels," in *Proceedings of Specialist Meeting on the Ultrasonic Inspection of Reactor Components*, Risley, England, September 1976; and Cook, R. V. Latimer, P. J., and McClung, R. W., "Flaw Measurement Using Ultrasonics in Thick Pressure Vessel Steel," Final Report on Contract No. W-7405-eng-26 prepared by Oak Ridge National Laboratory for the U.S. Nuclear Regulatory Commission, Oak Ridge, Tenn., August 1982.

Silk typifies the art's reliance upon only one type of wave mode in any given test, the art's preference for separated probes and its typical nonuse of the phenomena of mode conversion for flaw characterization. Specifically, Silk shows a transmitting transducer on a first shoe located on one side of the target area which beams an incident ultrasonic wave at the target area to produce a returning wave of the same mode received by a receiving transducer located on a second shoe located on the other side of the target area.

SUMMARY OF THE INVENTION

Ultrasonic testing methods and units for characterizing planar flaws in hard-to-inspect materials such as welded and cladded pipes containing intergranular stress corrosion cracks. The invention characterizes flaws with pitch-catch transducers positioned front to back on a single module. One module uses a bimodal transducer to transmit longitudinal and shear waves to produce, through surface wave mode conversion, reflection and diffraction, a triplet of associated longitudinal and shear wave signals received by another bimodal transducer. Another module uses pitch-catch transducers to produce a doublet of associated shear wave signals from diffraction of an incident longitudinal wave at the upper and lower extremities of underclad fatigue cracks. Another module uses pitch-catch transducers to produce a doublet of associated shear wave signals from diffraction of an incident shear wave at the upper and lower extremities of buried fatigue cracks. The signals are enhanced by multiple one sided cross focusing on preselected target areas in the test specimen and are cognizable by pattern recognition. Flaw charaterization results from the created linear relationship between signal separation and crack depth.

Receiving bimodal transducer A, due to its inclination angle of Alpha $\alpha_1 = 22°$ and its location at a distance in front of transducer B, receives only those waves that strike the entry surface at angles that direct the waves after refraction at the specimen-module boundary toward transducer A. This is a form of selective spatial filtering. Three signals are received;
(1) a tip-diffracted longitudinal wave $L_a$ at Gamma $\gamma_1 = 50°$, (2) a mode-converted longitudinal wave $L'_a$, at Beta $\beta_1=25°$ and (3) a base-reflected shear wave $S_a$ at Beta $\beta_1=25°$ The upper target area comprising the area of convergence of waves $L_b$ and $L_a$ and lower target area comprising the area of convergence of waves $S_b'$, M, $L_a'$ and $S_a$ are shown. It is understood that "upper" refers to the target area closer to the examination surface while "lower" refers to the target area further away from it. Further, the target areas shown in the figures are used to teach the concept of converging incident and received waves rather than to delimit the actual areas within which they cross. In actual practice the size, shape and location target areas will vary in accordance with a variety of factors. They will, however, for a given module, remain in their particular depth zone or zones from the examination surface. Test specimen thickness is denoted by h and crack depth as measured vertically from the crack base is denoted by d. The outer and inner diameters are OD and ID, respectively. The electrical connections between transducers A and B and the remainder of the test unit instrumentation i.e. at least a transmitter, a receiver and a display unit, are shown.

Figure 2:
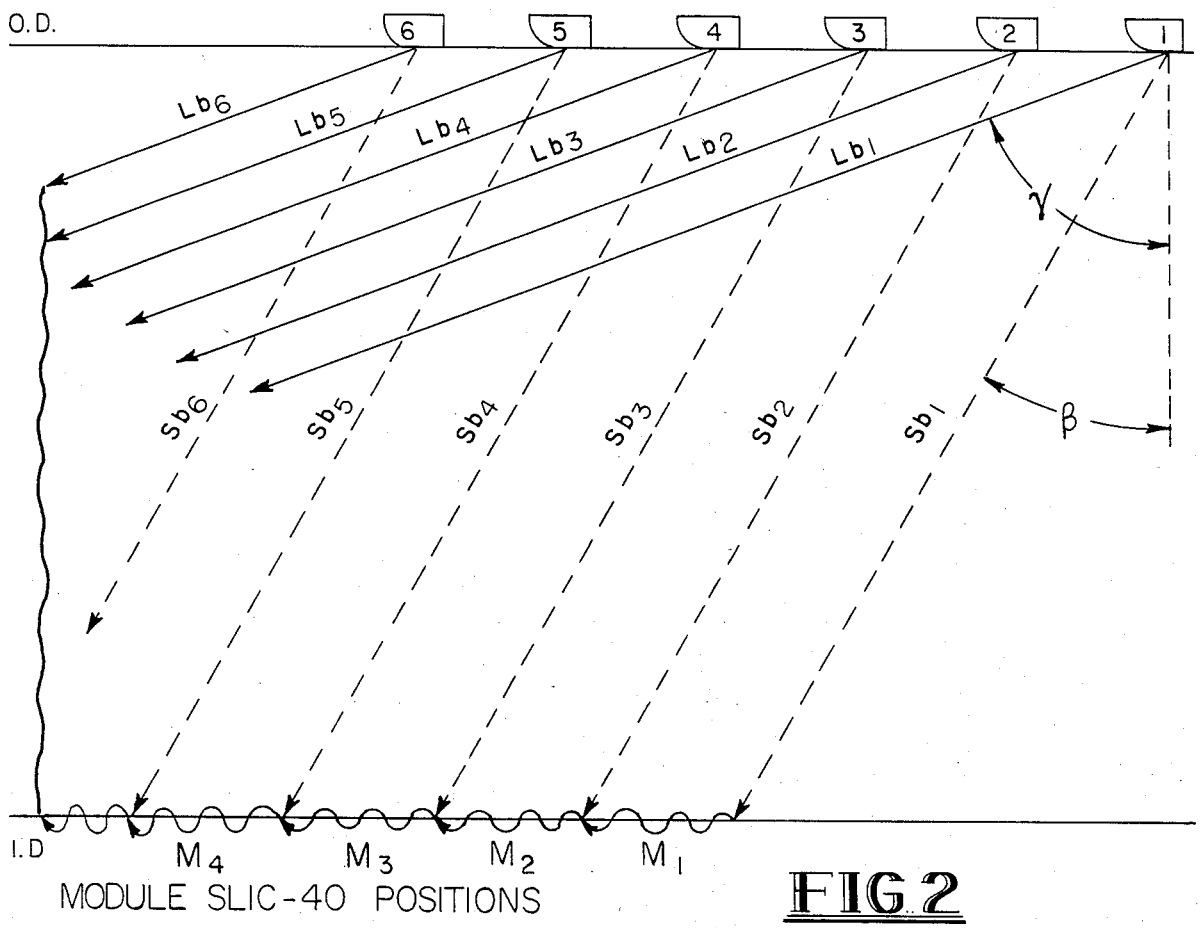

FIG. 2 shows various SLIC-40 module positions on a test specimen with a surface-connected crack. Transducer B transmits a shear beam $S_b$. The center of each numbered $S_b$ beam corresponds to the numbered module positions as shown. Probe B additionally transmits a longitudinal beam $L_b$. The center of each numbered $L_b$ beam corresponds to the numbered module positions as shown. The beam angles Beta $\beta$ and Gamma $\gamma$ for all module positions are deemed to be 30 degrees and 70 degrees, respectively. The mode-converted surface wave M created by the $S_{b2}$ beam travels to the crack base where it is mode converted into an $L_a'$ reflected beam (not shown).

Figure 3:
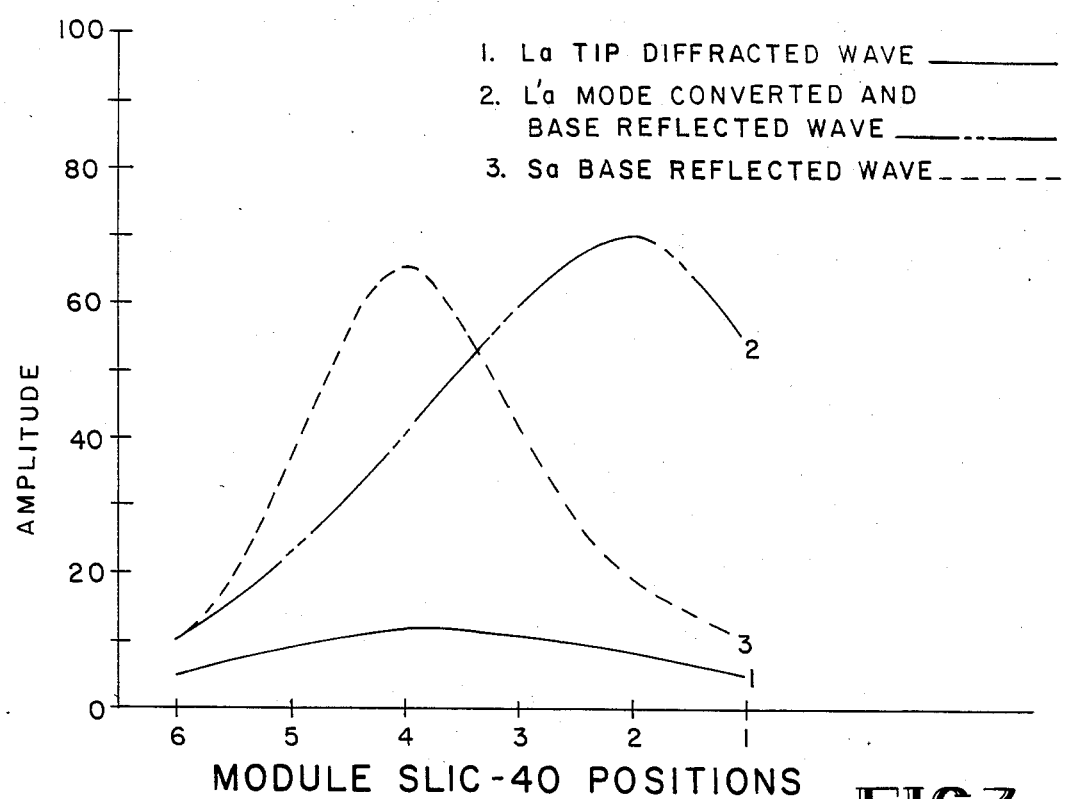
Figure 4A:
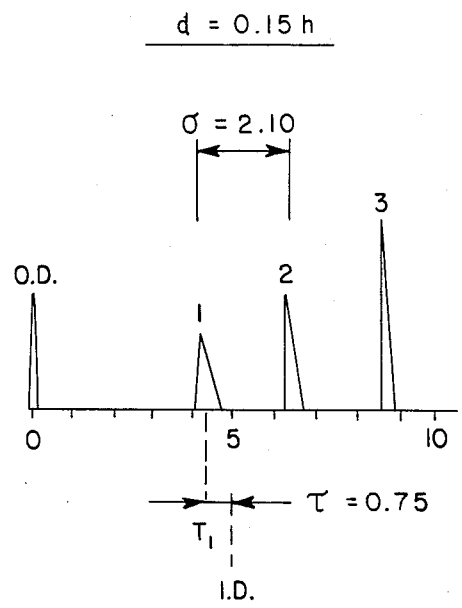
Figure 4B:
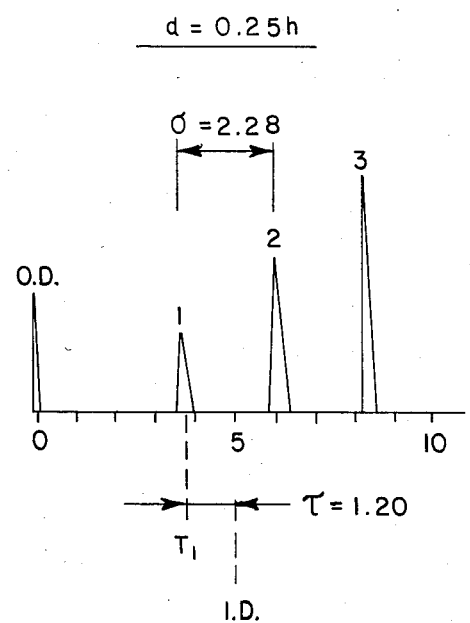
Figure 4C:
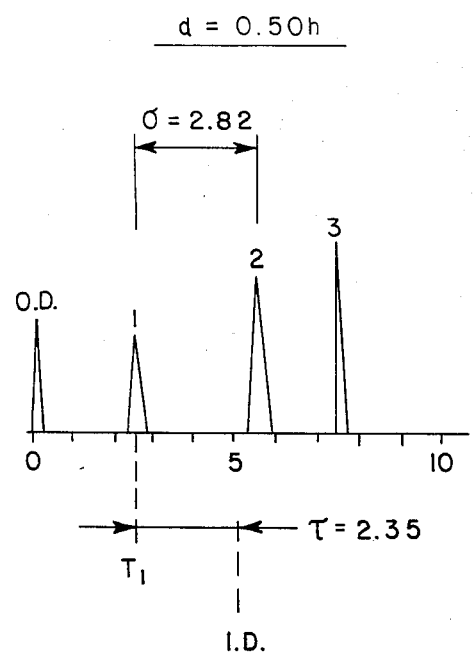
Figure 4D:
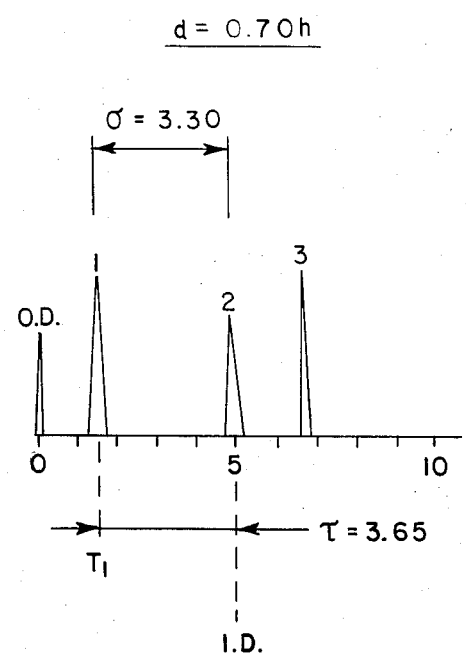

FIG. 3 shows the echo dynamic curves depicting the signal $L_a$ (pulse 1) due to the diffraction of the incident longitudinal wave $L_b$ at the crack tip, the signal $L_a'$ (pulse 2) due to mode conversion of the $S_b$ to a surface wave M and then through a second mode conversion to an $L_a'$ reflected wave, and the signal $S_a$ (pulse 3) due to the reflection at the crack base of the incident shear beam $S_b$, all with respect to the scanning of the SLIC-40 module as shown in FIG. 2 for a 50 percent deep surface-connected crack.

FIG. 4 shows experimental confirmation of the linear relationship between crack depth d and (1) doublet separation sigma $\sigma$ and (2) time delay tau $\tau$ obtained respectively by the two complementing techniques M-SPOT and M-PET. Pulse 1 corresponds to $L_a$, pulse 2 corresponds to $L_a'$ and pulse 3 corresponds to $S_a$. The tests were conducted with a SLIC-40 module located on the outer surface of a stainless steel block of 1 inch thick (h=25.4 mm) for simulated cracks connected to the inner surface of the block. The relative amplitudes, arrival times and time delay patterns of pulses 1, 2 and 3 as they are seen on a calibrated screen of a resolution unit and how the overall pattern changes in relation to increasing crack depths are shown for crack depths of 0.15h, 0.25h, 0.50h and 0.70h in FIGS. 4a, 4b, 4c and 4d, respectively. These characteristic patterns are used in the invented pattern recognition method of distinguishing and identifying pulses 1, 2 and 3 against the background interference caused by the clad-base and weld-base metal interfaces.

Figure 5:
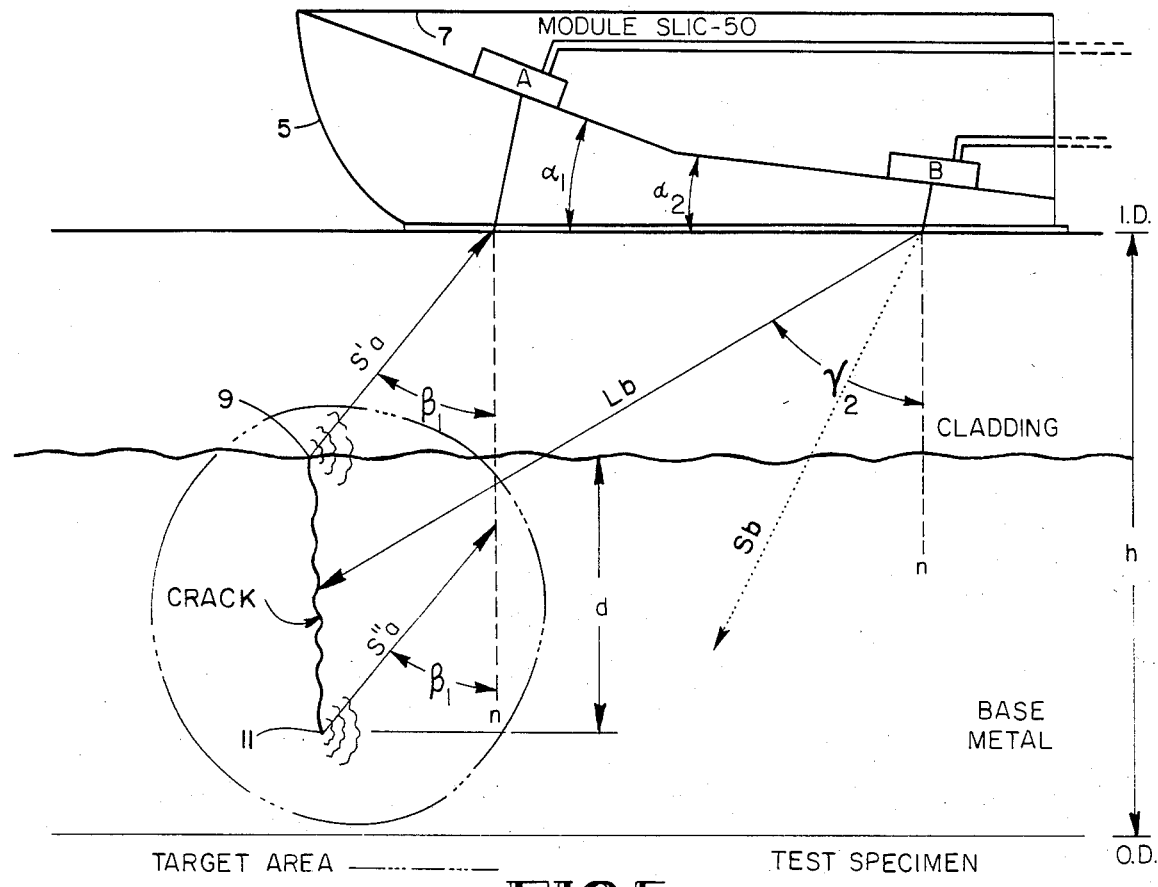

FIG. 5 shows a SLIC-50 module examining a cladded pressure vessel from the inner surface for an underclad fatigue crack originating at the clad-base metal interface near the weld. Bimodal transmitting transducer B transmits an incident longitudinal wave $L_b$ at gamma $\gamma_2=60°$ from line n perpendicular to the examination surface due to its inclination angle of alpha $\alpha_2=24°$. A shear wave is also transmitted from transducer B but this wave's reflections or diffractions are not received by transducer A because the incident shear wave $S_b$ is not aimed toward the target area.

$L_b$ is shown striking the crack and producing waves from the upper and lower extremities of the crack, $S_a'$ and $S_b''$, respectively. Due to the inclination angle of receiving transducer A (alpha $\alpha_1=34°$) and its location at a distance in front of transducer B, The $S_a'$ waves are received at an angle of approximately $B_1=40$ degrees.

The target area comprising the area of convergence of the incident wave $L_b$ and the returning waves $S_a'$ and $S_a''$ is shown. Test specimen thickness is denoted by h and crack depth is denoted by d. The outer and inner diameters are OD and ID respectively. The electrical connections between transducers A and B and the remainder of the test unit are shown.

Figure 6:
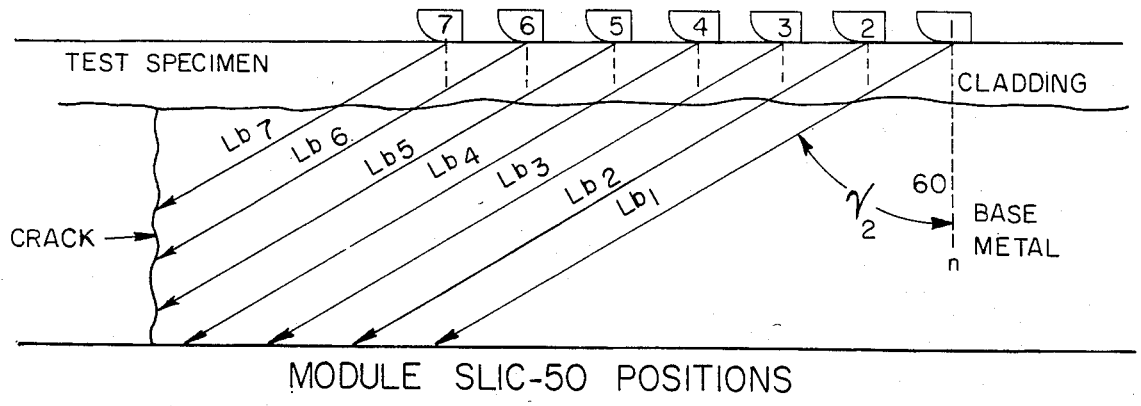

FIG. 6 shows various SLIC-50 module positions on a test specimen aimed at the different parts of an underclad fatigue crack. Transducer B transmits a longitudinal beam $L_b$. The center of each numbered $L_b$ beam corresponds to the numbered module positions as shown. The angle for each $L_b$ beam is deemed to be 60 degrees.

Figure 7:
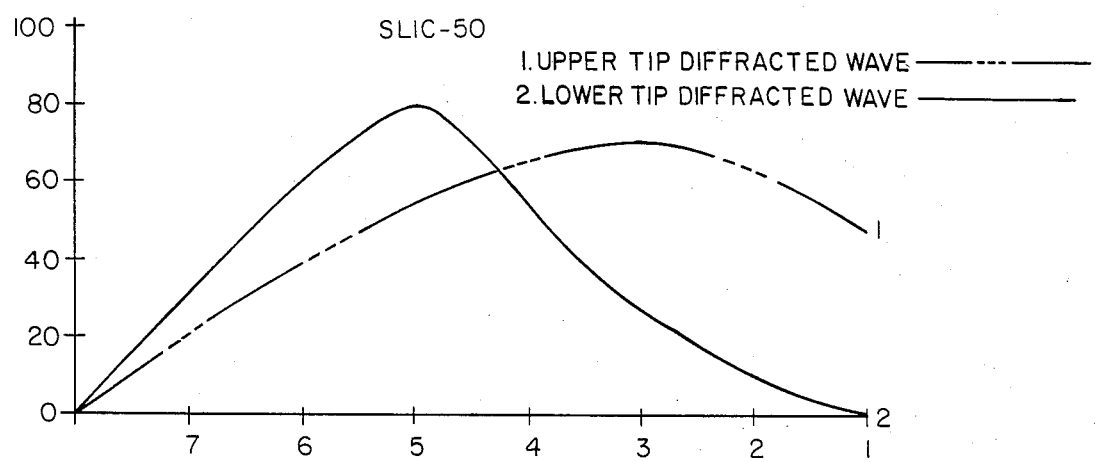

FIG. 7 shows the echo dynamic curves depicting the relative amplitudes of the signal $S_a'$ (pulse 1) originating from the upper crack extremity and the signal $S_a''$ (pulse 2) originating from the lower crack extremity with respect to the scanning of the SLIC-50 module as shown in FIG. 6 for a 13-mm deep underclad crack.

Figure 8A:
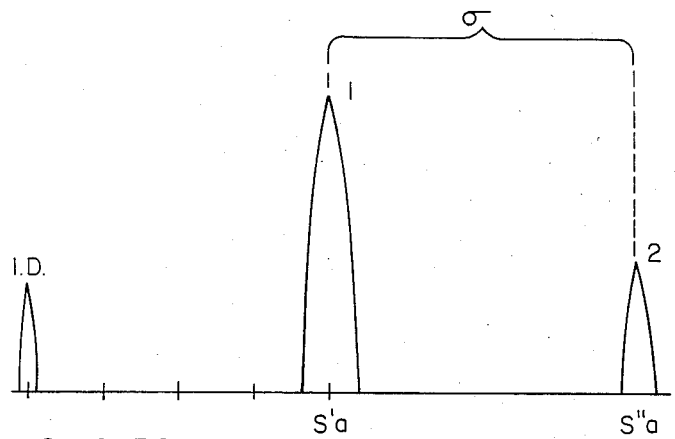
Figure 8B:
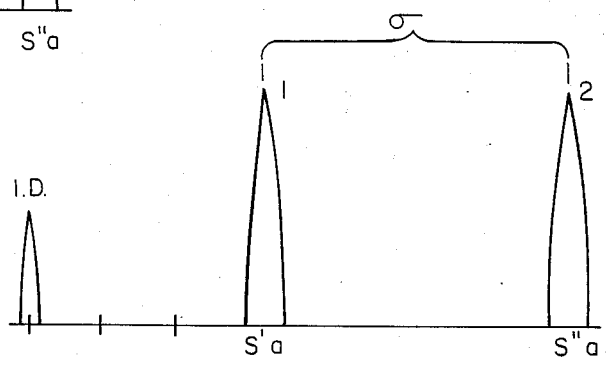
Figure 8C:
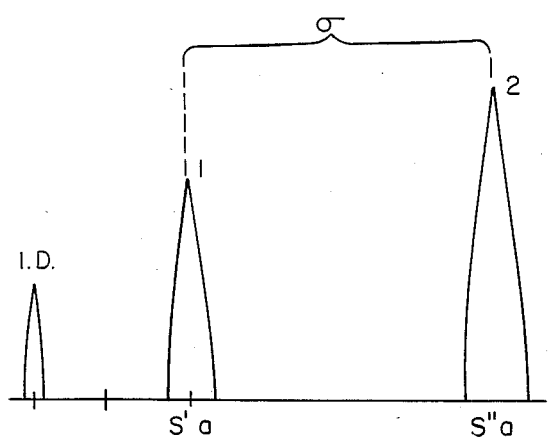

FIG. 8 screen presentations show the independence of doublet separation sigma $\sigma$ from module position and the characteristic asynchronous dependence of the pulse amplitudes on module position. These presentations show the relative times of arrival, the constant doublet separation and the dynamic amplitude pattern of pulses 1 and 2 produced by the SLIC-50 module for the described underclad crack. These characteristic features are used collectively in the invented pattern recognition method of distinguishing and identifying the $S_a'$ and $S_a''$ signals against the background interference caused by the clad-base and weld-base metal interfaces. The display screen presentations corresponding to SLIC-50 module positions 3, 4 and 5 of FIG. 6 are shown in FIGS. 8a, 8b and 8c.

Figure 9:
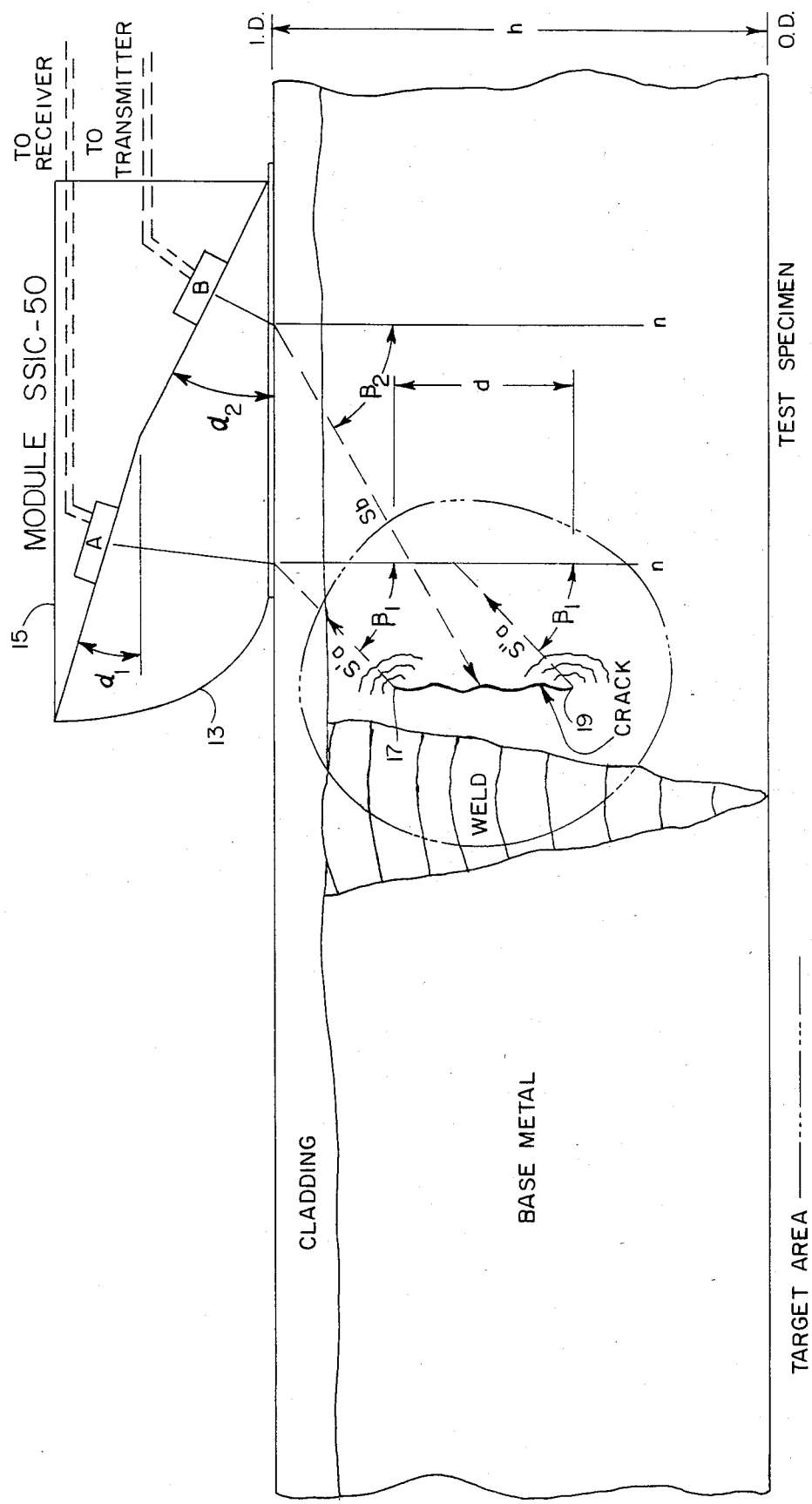

FIG. 9 shows a SSIC-50 module examining a cladded pressure vessel from the inner surface for a buried fatigue crack near midwall in the vicinity of a weld. Transmitting transducer B transmits an shear beam $S_b$ at Beta $\beta_2=60°$ from line n perpendicular to the examination surface due to its inclination angle of Alpha $\alpha_2=48°$.

$S_b$ is shown striking the crack and producing diffracted waves from the upper and lower extremities of the crack, $S_a'$ and $S_a''$, respectively. Due to the inclination angle of receiving transducer A (Alpha $\alpha_1=37°$) and its location a distance in front of tranducer B, the $S_a'$ and $S_a''$ waves are received at an angle of approximately Beta $\beta_1=45°$.

The target area comprising the area of convergence of incident wave $S_b$ and received waves $S_b$ and $S_a''$ is shown. Test specimen thickness is denoted by h and crack depth is denoted by d. The outer and inner diameters ar OD and ID respectively. The electrical connections between transducers A and B and the remainder of the test unit are shown.

Figure 10:
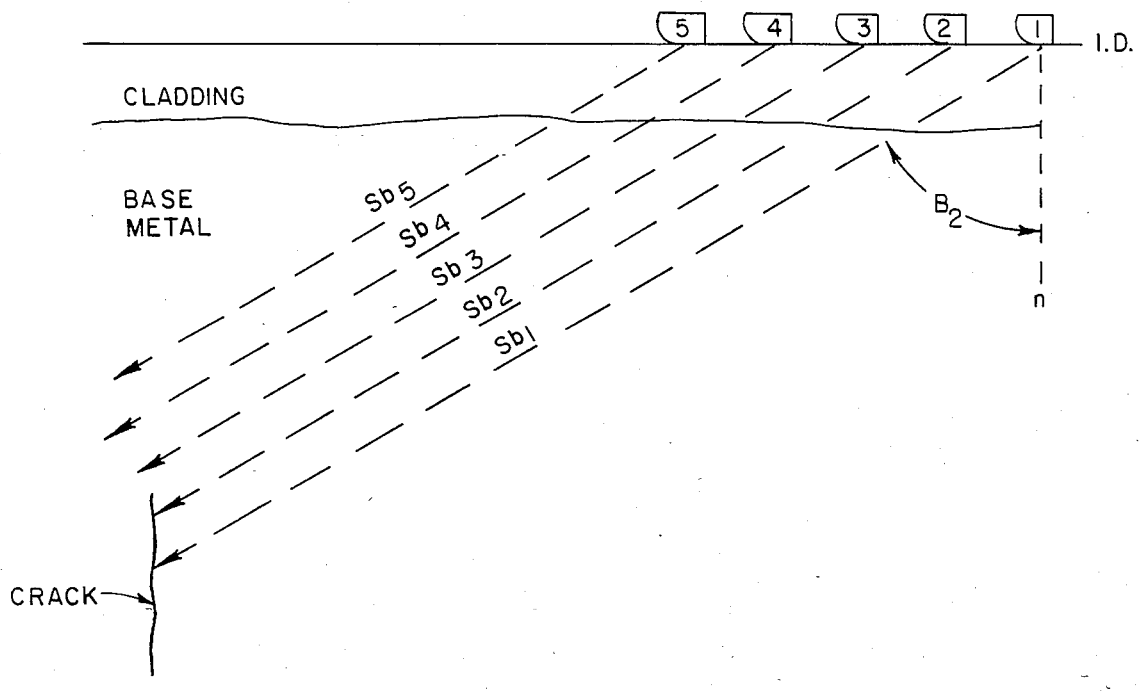

FIG. 10 shows SSIC-50 various module positions on the test specimen aimed at the different parts of a buried fatigue crack. Transducer B transmits a shear beam $S_b$. The center of each numbered $S_b$ beam corresponds to the numbered module positions as shown. The angle for each beam is deemed to be 60 degrees.

Figure 11:
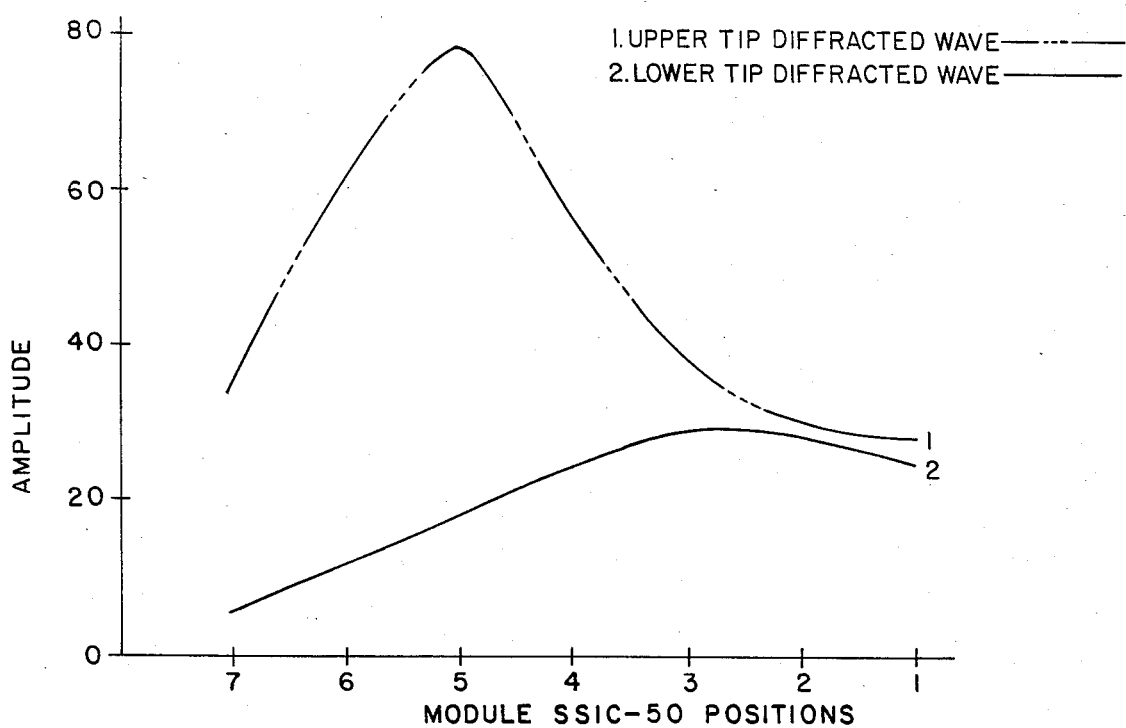

FIG. 11 shows the echo dynamic curves depicting the relative amplitudes of the signal $S_a'$ (pulse 1) originating from the upper crack extremity and the signal $S_a''$ (pulse 2) originating from the lower crack extremity with respect to the scanning of the SSIC-50 module as shown in FIG. 10 for a 10-mm deep buried crack.

Figure 12A:
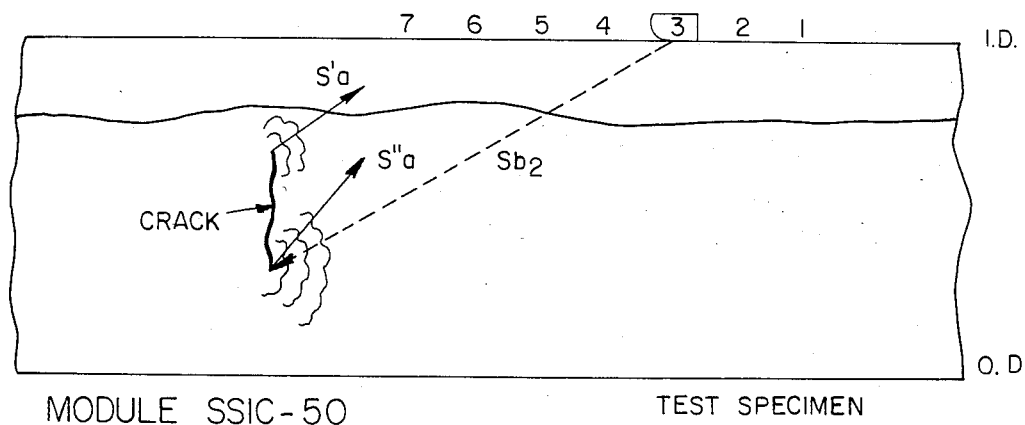
Figure 12B:
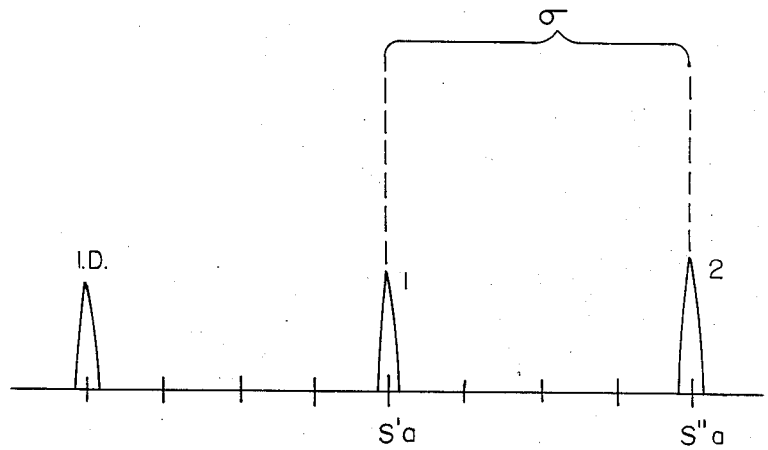

FIG. 12 shows the independence of doublet separation Sigma $\sigma$ from module position and the characteristic asynchronous dependence of the pulse amplitudes on module position. FIGS. 12a, 12c and 12e show the SSIC-50 module aimed at the lower extremity, center and upper extremity of the crack at module positions 3, 4 and 5, respectively. The corresponding screen presentations are shown in FIGS. 12b, 12d and 12f. These presentations show the relative times of arrival, the constant doublet separation and the dynamic amplitude pattern of pulses 1 and 2 produced by the SSIC-50 module for the described buried crack. These characteristic features are used collectively in the invented pattern recognition method of distinguishing and identifying the $S_a'$ and $S_a''$ signals against the background interference caused by the clad-base and weld-base metal interfaces.

DESCRIPTION OF THE PREFERRED EMBODIMENT

The inspection difficulties described above are partially due to the fact that ultrasonic shear waves do not effectively interact with the upper extremities (tips) of intergranular stress corrosion cracks in the heat affected zones of austenitic piping welds to produce readily observable satellite pulses for crack sizing purposes and that ultrasonic longitudinal waves do not, standing alone, produce readily recognizable and useful signals from crack base reflectors under such conditions. Grazing longitudinal waves, on the other hand, interact effectively with the tips of such cracks while shear waves interact well with the crack base. The SLIC-40 module of the Multibeam Satellite-Pulse Observation Technique (M-SPOT) method and test unit described herein uses longitudinal waves to interact with both crack extremities and shear waves to interact with the crack base to produce signals which are readily recognizable in spite of the low signal-to-background ratios caused by the clad-base and weld-base metal interfaces and which are useful to locate, identify and size the crack.

The SLIC-40 module improves the signal-to-background ratio by novel combinations of bimodal transducers to produce through multiple one sided cross focusing enhanced associated signals, which collectively result in an easily discernable pulse pattern comprised of predictable times of arrival, a constant pulse separation and characteristic relative amplitude patterns. To accomplish this for different flaw types and different flaw locations various transducer modules can be designed which use the multiple one sided cross focusing and pattern recognition concepts for flaw characterization taught herein.

Multiple one sided cross focusing of multiple transmitted and/or multiple returned beams by means of pitch-catch transducers located in a single module which is operable from one side of a flaw, is novel to the invention. The concept is implemented through the invention's placement of transmitting and receiving transducers in back and in front of each other in a single module and angling them to take advantage of their capacity for bimodal operation by aiming their different beams to cross in areas of interest in the test specimen or target areas. As will be discussed and shown more fully below, "multiple" refers to the invention's cross focusing of beams on more than one target area. "One sided" refers to the invention's ability to produce results from only one side of the flaw, typically from a single module. "Cross focusing" refers to the angling of the transmitting and receiving transducers to direct their beams to intersect in areas of interest within the test specimen. Angling the receiving transducer to only receive ultrasonic waves striking the entry surface-module boundary at a selected location and at a selected angle limits the received ultrasonic waves to those originating in at the target area. This excludes ultrasonic reflections, diffractions, etc. (interference) from regions outside the target area. Thus electronic pulses or signals due to the reflections, diffractions, etc. produced within the target area are enhanced relative to those produced by other test methods such as the pulse echo method. Those of ordinary skill in the art will appreciate that the "flaw" being inspected may be any anomaly within the test specimen which is capable of usefully reflecting incident waves as described herein.

Those of ordinary skill in the art will appreciate that either the forward transducer, shown herein as transducer A, or the back transducer, shown herein as transducer B, may be the transmitting or receiving transducer. Indeed, to facilitate modifying the SLIC and SSIC modules shown herein to adapt the invention to different test specimens both transducers can be thought of as transmitting and the target area be calculated as the area within the test specimen in which the beams intersect.

Figure 1:
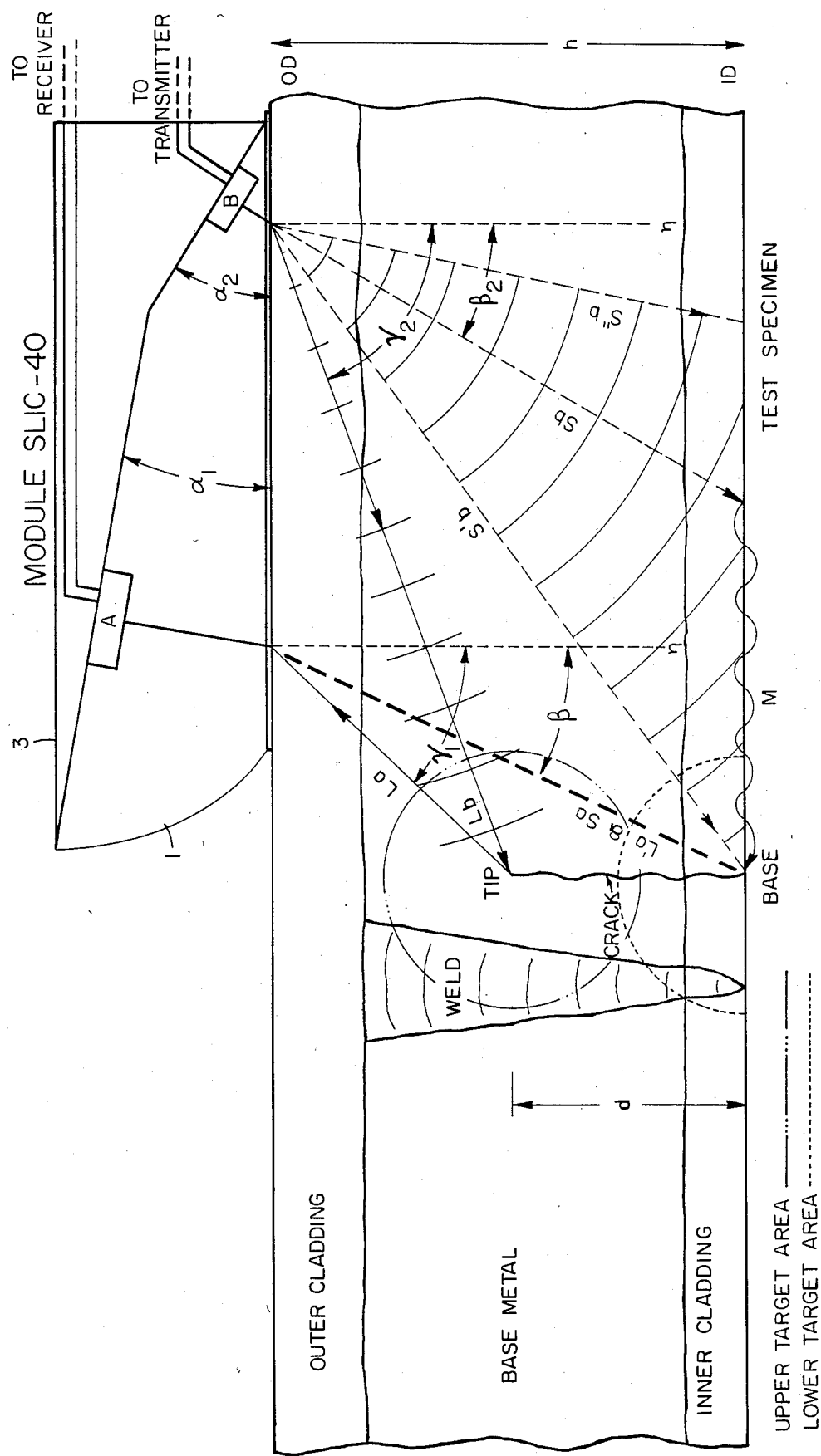
FIG. 1 shows a SLIC-40 module examining a double cladded and welded pipe from the outer surface for Intergranular Stress Corrosion Cracks (IGSCC) or other planar flaws near the weld. Transmitting bimodal transducer B due to its inclination angle of alpha $\alpha_2 = 27°$ transmits an ultrasonic incident shear wave $S_b$ at Beta $\beta_2 = 30°$ from line n perpendicular to the examination surface of the test specimen and an ultrasonic incident longitudinal wave $L_b$ at Gamma $\gamma_2 = 70°$. A surface wave M resulting from mode conversion of $S_b$ upon its striking the test specimen's far suface and propagating toward the crack's base where a second mode conversion produces therefrom an $L_a'$ wave is shown. A left part of the spreading $S_b$ beam $S_b'$ is shown striking the base of the crack while its right part, $S_b''$, is shown striking the test specimen's far surface. The $L_b$ beam strikes the upper extremity of the crack.

The bimodal SLIC-40 module is a non-planar two-element transducer array mounted on a single shoe. Module is used herein to describe at least two transducers mounted on a common shoe with a roof angle greater than zero degrees between them. A roof angle is the absolute value of the difference between the inclination angles alpha $\alpha$ and alpha $\alpha_2$. Three associated and enhanced signals or pulses (a triplet) are obtained when bimodal transducer B transmits and bimodal transducer A receives or vice-versa. The first pulse (pulse 1) originates by diffraction of the incident $L_b$ wave from the upper crack extremity to produce the $L_a$ beam as shown in FIG. 1. The second pulse (pulse 2) originates from the mode conversion of the incident $S_b$ wave at the inner surface of the specimen to a surface wave M which travels to the crack base where it is again mode converted and reflected to produce the $L_a'$ beam as shown in FIG. 1. The third pulse (pulse 3) originates from the reflection of the $S_b$ wave from the crack base to produce the $S_a$ beam as shown in FIG. 1. Thus, pulse 1 originates from the crack tip while pulses 2 and 3 originate from the crack base.

Pulses 1, 2 and 3 are associated meaning that (1) their sequence of arrival is independent of module-to-flaw distance and test specimen composition, (2) the differences in their times of arrival are substantially independent of these factors and (3) their relative amplitudes have a characteristic relationship to each other as the moducle is scanned about the flaw. The linear relationship between crack depth and pulse 1-pulse 2 and pulse 1-pulse 3 separations is shown in FIG. 4. Because more reliable measurements are obtained from the pulse 1-pulse 2 separation it is the one preferably used. FIG. 4 shows pulses 1, 2 and 3 for peaked pulse 1 module positions and also shows that the greater the crack depth d the larger the pulse 1-pulse 2 separation and the amplitude of the peaked pulse 1 relative to those of pulses 2 and 3. When the transducers are arranged in a module as shown in FIG. 1, pulse 1 acts as a preceding satellite of pulse 2 since their time delay (doublet separation sigma $\sigma$) is practically independent of the axial coordinate (X) of the module relative to the crack's X coordinate and pulse 1 invariably precedes pulse 2. The ultrasonic examiner is thus able to locate the pulse 1-pulse 2 associated pair in spite of the substantial clad and/or weld caused interference by scanning the SLIC-40 module about the region of interest containing the suspected crack and observing the pulses that appear to travel together on the instrument screen as if rigidly joined. A useful feature of the invention is that module can be anywhere along the test specimen as long as both the first and second pulses can be identified due to their relative amplitude pattern and movement in unison and can be resolved at the same time.

Pulse 1 is received before pulse 2 because of two reasons; (1) the $L_b+L_a$ path is shorter than the $S_b+M+L_a'$ path and (2) the velocity of longitudinal waves is greater than that of shear waves. Pulse 2 is received before pulse 3 because of the greater velocity of the reflected $L_a'$ wave as compared to that of reflected $S_a$ wave.

Given sufficient signal amplitudes to recognize the signals as a pair of constant separation, the invention method is independent of signal amplitude. The relative amplitude envelopes for the pulses suspected of being the $L_a$, $L_a'$ and $S_a$ signals must be similar to the asynchronous echo dynamic curves shown in FIG. 3. Both the separation of the pulses and their relative amplitudes depend on crack depth. The echo dynamic curves are obtained by scanning or moving the SLIC-40 module about the suspected crack and observing the effect of module position on the sequence of arrival of the candidate pulse pairs, their separations and relative amplitudes. A candidate pulse pair is any pair of pulses which, due to their relative amplitudes and times of arrival may possibly be an indication from a flaw in the test specimen. The candidate pair may be pulses 2 and 3, pulses 1 and 2 or pulses 1 and 3. To facilitate crack detection, the examiner may initially look for the pulse 2-pulse 3 doublet and, in particular, the typically stronger pulse 2 by scanning the SLIC-40 module over the region of interest. When the examiner observes a candidate pulse the module is moved back and forth in fine steps in search of an associated pulse to confirm the presence of a crack. Confirmation uses the known relationship between the pulses 2 and 3, i.e. their constant sequence of arrival, constant time delays and characteristic relative amplitude patterns. Pulse 1 must be observed for crack sizing.

The term SLIC was chosen for these invention modules as they use Shear and Longitudinal waves to Inspect or Identify and Confirm or Characterize flaws.

The above SLIC module has been named the SLIC-40 module for identification purposes as the average of the two transmitted beam angles and the two received beam angles (870°+50°+30°+25°]÷4) is approximately 40°. Those skilled in the art will appreciate that the SLIC-40 module is representative of similar modules which can be usefully designed using the invented concepts.

For test specimens comprised of steel and wedges comprised of lucite, the inclination angle Alpha $\alpha$ for a bimodal transducer may not be larger than 29°. Probes with inclination angles larger than alpha equals 29° will not generate longitudinal waves of sufficient energy within the test specimen. Any inclination angle alpha $\alpha$ between 0° and 29° may be used although alpha $\alpha$ angles in the range of 18° to 27° are preferable for bimodal transducers. FIG. 1 shows transducers A and B mounted on shoe 1 and contained within casing 3. The Beta $\beta$ and Gamma $\gamma$ refraction angles of the invention are accurate only within ±3 degrees. Because neither of the transducers is focused the incident and returning beams spread sufficiently to overlap in large useful target areas. Further, use of Snell's law permits refraction angles Beta $\beta$ and Gamma $\gamma$ to be calculated by those skilled in the art for different desired depth zones in the specimen than those optionally examined by the SLIC-40.

The amplitude ratio is partially dependent on the alpha $\alpha$ angle of the transmitting transducer which apportions the incident ultrasonic energy between longitudinal and shear waves. Because the $S_b$ beam suffers greater propagation loss in a typical cladded specimen than does the $L_b$ beam the preferred value of the inclination angle for transducer B varies inversely with the thickness of the test specimen. The thicker the test specimen, the smaller the preferred value of the inclination angle.

The inclination angle Alpha $\alpha_1$ and Alpha $\alpha_2$ are chosen such that the transmitted beams $L_b$ and $S_b$ and received beams $L_a$ and $S_a$ are cross focused through the target areas within the test specimen. The signal-to-background ratio is enhanced through this cross focusing action as the energy received by transducer A can only come from the small upper target area within which the upper incident and returned beams cross and the small lower target area within which the lower incident and returned beams cross. Thus a design criterion for selecting inclination angle alpha 1 for transducer A is that it be angled to accept the useful returns from the upper and lower target areas. It will be appreciated by those skilled in the art that within the above guidelines, appropriate inclination angles may be selected for transducers A and B to move the target areas within test specimens of varying thickness, composition and flaw types and locations.

Furthermore, the probes of the SLIC-40 module may be used individually for pulse-echo insonifying of the test specimen as is taught in the referenced applications and the prior art.

Practically any wideband ultrasonic transducer may be used in the SLIC-40 module as transducer A or B. The transmitted pulses are preferably shorter than 2 cycles. The preferred embodiment uses moderately damped 4 MHZ transducers within the SLIC-40 module that have been manufactured by Southwest Research Institute of San Antonio, Tex.

The boat like shape or negative slope of the left side of the SLIC-40 module as shown in FIG. 1 is designed to accomodate transducers A and B within the module and also permit the module to be moved over the edge of a weld crowns that may obstruct the examination surface to maximize the time over which pulses 1 and 2 can be simultaneously seen for cracks adjacent to the weld.

A couplant solution typically comprised of a light oil is applied to the bottom of the module prior to use to facilitate transmission of the ultrasonic energy from the lucite shoe into the test specimen.

Because the entire thickness of the test specimen is scanned by the two probes of the SLIC-40 module the invention is applicable for sizing small and large cracks.

Calibration of the test instrument is necessary for crack sizing. Calibration for M-SPOT and M-PET uses a stepladder calibration block containing a series of end-milled notches with upper extremities (tips) 5, 10, 15, ... 35 mm below the examination surface. A series of maximized notch-tip diffracted signals (i.e., the first pulses) are used to calibrate the time base of the ultrasonic instrument for a given degraded pipe application. For both multibeam sizing techniques, the time base is calibrated in throughwall distance, i.e, in percent of pipe wall thickness rather than metal path. The range control and the material calibration and delay dials of the instrument are adjusted so that each major horizontal screen division corresponds to 20 percent of the thickness of the pipe at the crack location (local pipe wall thickness, $h_x$). That is, the beam entry point on the OD (at $Z=O$) is placed at the extreme left side of the screen as in FIG. 4 and the ID (at $Z=h$) is placed at the center of the horizontal screen (see pulse 5 in FIG. 4). Since pulse 5 is fictitious, pulse 2 from the detected crack is placed after peaking, at 60 percent of full screen width (i.e., at the sixth division mark). When the instrument is properly calibrated for the local pipe wall thickness, the separation between the peaked pulse 2 and the not-necessarily peaked pulse 3 should be 2.0 divisions. The value of $h_x$ can then be read from nomograms prepared in the laboratory prior to the field work using the range, material calibration and delay dial settings of the instrument calibrated for the crack in question. If the local pipe wall thickness is already known, then the nomograms can be used to quickly calibrate the instrument for Sigma $\sigma$ and Tau $\tau$ measurements to permit a direct readout of the flaw depth d from the screen presentation.

The instrument gain for scanning is typically such that the average background interference level is ten percent of full screen height.

If it is possible to peak the amplitude of pulse 1 an additional sizing method may be employed and its results combined with the M-SPOT results. The travel time of the peaked pulse 1 is denoted by T in FIG. 4. The delay time tau $\tau$ measured between the peaked tip-diffracted pulse (pulse 1) and a fictious diffracted pulse from the crack base that would peak at screen division 5 (pulse 5) also provides a linear correlate of crack depth. The crack depth obtained by this Multibeam Peak-Echo Technique (M-PET) can be compared to that obtained by the M-SPOT and the larger of the two depth estimates should be reported to be conservative.

The SLIC-50 module shown in FIG. 5 is a variation of the SLIC-40 module. While it also uses the invented one sided cross focusing it is different in design and use due to its primary purpose being the detection and characterization of under-clad cracks.

FIG. 5 shows a SLIC-50 module examining a cladded pressure vessel from the inner surface for an underclad fatigue crack originating at the clad-base metal interface near the weld. Bimodal transmitting transducer B transmits an incident longitudinal wave $L_b$ at gamma $\gamma_2=60°$ from line n perpendicular to the examination surface due to its inclination angle of alpha $\alpha_2=24°$. A shear wave is also transmitted from transducer B but this wave's reflections or diffractions are not received by transducer A because the incident shear wave $S_b$ is not aimed toward the target area.

$L_b$ is shown striking the crack and producing waves from the upper and lower extremities of the crack, $S_a'$ and $S_a''$, respectively. Due to the inclination angle of receiving transducer A (alpha $\alpha_1=34°$) and its location at a distance in front of transducer B, the $S_a'$ waves are received at an angle of approximately $B_1=40$ degrees.

The target area comprising the area of convergence of the incident wave $L_b$ and the returning waves $S_a'$ and $S_a''$ is shown. Test specimen thickness is denoted by h and crack depth is denoted by d. The outer and inner diameters are OD and ID respectively. The electrical connections between transducers A and B and the remainder of the test unit are shown.

FIG. 6 shows various SLIC-50 module positions on a test specimen aimed at the different parts of an underclad fatigue crack. Transducer B transmits a longitudinal beam $L_b$. The center of each numbered $L_b$ beam corresponds to the numbered module positions as shown. The angle for each $L_b$ beam is deemed to be 60 degrees.

FIG. 7 shows the echo dynamic curves depicting the relative amplitudes of the signal $S_a'$ (pulse 1) originating from the upper crack extremity and the signal $S_a''$ (pulse 2) originating from the lower crack extremity with respect to the scanning of the SLIC-50 module as shown in FIG. 6 for a 13-mm deep underclad crack.

FIG. 8 screen presentations show the independence of doublet separation sigma $\sigma$ from module position and the characteristic asynchronous dependence of the pulse amplitudes on module position. These presentations show the relative times of arrival, the constant doublet separation and the dynamic amplitude pattern of pulses 1 and 2 produced by the SLIC-50 module for the described underclad crack. These characteristic features are used collectively in the invented pattern recognition method of distinguishing and identifying the $S_a'$ and $S_a''$ signals against the background interference caused by the clad-base and weld-base metal interfaces.

The SLIC-50 module is useful for crack detection and sizing for broad depth ranges. Prior art dual element probes used for crack detection are amplitude dependent and are incapable of sizing. They are grazing longitudinal beams to cross focus on a upper crack tip by moving a module having side by side transducers, one with a positive slope and the other with a negative slope, directly over it. Because of the extremely severe focusing required by this method the roof angles between the transducers on such probes are in the range of from one degree to four degrees, the depth zone within which a single modulle can give reliable results is less than approximately 10 mm thick and the maximum range within which they can reliably test is approximately 1 inch. The SLIC-50 module uses multiple wave modes and transducers which each have a positive slope. Thus the SLIC-50 module does not have to be directly over a crack to detect or size it but rather can be moved toward the crack from any available direction. The longer metal path caused by approaching flaws from a side angle rather than from directly above permits any given SLIC-40 module to inspect thick depth zones which expand as the region of interet at which the SLIC-40 module is aimed is moved further within the test specimen. The large roof angle used in the SLIC-40 module, up to 15 degrees, permits reliable cross focusing and gives the invented method a usefulness at great ranges within a test specimen, preferably no more than approximately 1 inch.

A mere catagorizing of the structural differences of the SLIC-50 module from the prior art is insufficient, however, to covey the difference in concept between the invention's reliance on pulse separation based pattern recognition for detection and pulse separation alone for sizing. The amplitude based prior art methods are unreliable in the field even within their narrow useful zones and ranges as the critical looked for amplitudes are practically or completely obstructed by background interference in difficult to inspect specimens and are so short lived when produced by a scanning modulle as to be easy to miss. Basing the invention method on pulse separation completely relives the method of any reliance on amplitude given sufficient amplitude discriminate between pulses and permit the examiner to find the associated pulse pair and produces a long lived information bearing associated pulse pair. Thus the associated pulse pair is much more reliably found than a single pulse amplitude when a flaw exists in a difficult to inspect test specimen.

FIG. 9 shows a SSIC-50 module examining a cladded pressure vessel from the inner surface for a buried fatigue crack near midwall in the vicinity of a weld. Transmitting transducer B transmits an shear beam $S_b$ at Beta $\beta_2=60°$ from line n perpendicular to the examination surface due to its inclination angle of Alpha $\alpha_2=48°$.

$S_b$ is shown striking the crack and producing diffracted waves from the upper and lower extremities of the crack, $S_a'$ and $S_a''$, respectively. Due to the inclination angle of receiving transducer A (Alpha $\alpha_1=37°$) and its location a distance in front of transducer B, the $S_a'$ and $S_a''$ waves are received at an angle of approximately Beta $\beta_1=45°$.

The target area comprising the area of convergence of incident wave $S_b$ and received waves $S_b$ and $S_a''$ is shown. Test specimen thickness is denoted by h and crack depth is denoted by d. The outer and inner diameters are OD and ID respectively. The electrical connections between transducers A and B and the remainder of the test unit are shown.

FIG. 10 shows SSIC-50 various module positions on the test specimen aimed at the different parts of a buried fatique crack. Transducer B transmits a shear beam $S_b$. The center of each numbered $S_b$ beam corresponds to the numbered module positions as shown. The angle for each beam is deemed to be 60 degrees.

FIG. 11 shows the echo dynamic curves depicting the relative amplitudes of the signal $S_a'$ (pulse 1) originating from the upper crack extremity and the signal $S_a''$ (pulse 2) originating from the lower crack extremity with respect to the scanning of the SSIC-50 module as shown in FIG. 10 for a 10-mm deep buried crack.

FIG. 12 shows the independence of doublet separation Sigma from module position and the characteristic asynchronous dependence of the pulse amplitudes on module position. FIGS. 12a, 12c and 12e show the SSIC-50 module aimed at the lower extremity, center and upper extremity of the crack at module positions 3, 4 and 5, respectively. The corresponding screen presentations are shown in FIGS. 12b, 12d and 12f. These presentations show the relative times of arrival, the constant doublet separation and the dynamic amplitude pattern of pulses 1 and 2 produced by the SSIC-50 module for the described buried crack. These characteristic features are used collectively in the invented pattern recognition method of distinguishing and identifying the $S_a'$ and $S_a''$ signals against the background interference caused by the clad-base and weld-base metal interfaces.

The discussion of the SLIC-50 module's differences and advantages over the prior art is similar to those of the SSIC-50 module. The SSIC method uses Shear and Shear waves to Inspect or Identify and Confirm or Characterize flaws. The design changes of the SSIC modules from the SLIC modules are to increase the invented methods range within the test specimen. While the SSIC-50 module may be used for deeper range, the depth zones within which its area is moved through is preferably more than one half inch and less than eleven inches into the test specimen from its examination surface.

It will be understood by those skilled in the art that the invented transducer modules can be used with other multiple beam and single beam flaw detection or characterization methods and that the invention, rather than adding a single additional tool to the examiner's repertoire, synergistically combines with the other methods to produce more reliable and conveniently obtained results.

The better multiple one sided cross focusing signal enhancement relative to prior art pulse-echo testing is due to the pulse echo incident and received beams traveling through the same metal path while the invention incident and received waves travel through different metal paths. Thus any cladding, material inhomogenities, benign flaws and other interference causing items located between a pulse echo transducer and its target area are reflected back to the transducer in combination together with the flaw indicating signal in pulse echo methods. In tests according to the invention, however, the transmitting and receiving transducer beams are positioned behind and in front of each other and angled so their transmitted and received beams respectively only intersect in the preselected target area. Thus cladding, material inhogenities, benign flaws, etc. encountered by the transmitted wave prior to reaching the target area do not cause interference against the signals returned to the receiving transducer because they are not received by the receiving transducer.

The invented method's use of pattern recognition and pulse separation-measurement frees it from dependence on returning pulse amplitude, absolute time measurements and module to flaw distance measurements. Further advantages of the invention are that the same mix of shear and longitudinal waves can be used for detection, identification/confirmation and sizing of flaws, the various pulses used for measurement are enhanced by the method to provide a good signal to background ratio, crack sizing can be done through welds and cladding, flaw size can be read directly or indirectly from the resolution unit, the doublet separation measurements as can be performed even when there is a wide weld crown, reliability of the M-SPOT sizing technique alone is acceptable and absolute arrival time measurements can provide confirmatory size information.

The advantages apparent in the above description are significant improvements in the art of nondestructive testing. While the invention has been described in connection with the preferred embodiment, it is not intended to limit the invention to the particular forms set forth, but, on the contrary, is intended to cover such alternatives, modification and equivalents as may be included within the spirit and scope of the invention as defined by the appended claims.

I claim:

1. An ultrasonic test method of determining the depth of a flaw in a test specimen from a single examination surface of said test specimen comprising:

transmitting into said test specimen by means of a first transducer a first incident wave directed at an upper target area within said test specimen;

receiving from said upper target by means of a second transducer located on the same side of said target area as said first transducer and having a different angular orientation to said examination surface than said first transducer a first returned wave and converting said first returned wave to a first signal;

transmitting into said test specimen by means of said first transducer a second incident wave directed at a lower target area located below said upper target area;

receiving from said lower target area by means of said second transducer a second returned wave and converting said second returned wave to a second signal;

simultaneously displaying by means of a display unit said first and second signals;

moving said first and second transducers along said examination surface;

recognizing said first and second signals as comprising a doublet of associated signals from a flaw located in said upper and lower target areas if, upon movement of said first and second transducers, said first signal's sequence of arrival remains prior to said second signal's sequence of arrival and the first separation comprised of the difference between said first signal's time of arrival and said second signal's time of arrival is substantially independent of the distance between said upper and lower target areas and said first and second transducers;

measuring said first separation;

determining said flaw's depth by using said first separation as a proportional indicator of flaw depth.

2. An ultrasonic test method of determining the depth of a flaw in a region of interest in a test specimen from a single examination surface comprising:

transmitting into said region of interest by means of a first transducer a first incident wave comprised of an ultrasonic longitudinal wave and a second incident wave comprised of an ultrasonic shear wave, said first incident wave having a larger angle with said examination surface than said second incident wave and said second incident wave having an angle greater than zero;

producing a first returning wave comprised of a longitudinal wave diffracted from an upper extremity of said flaw, a second returning wave comprised of a shear wave reflected from a lower extremity of said flaw and a third returning wave comprised of a mode-converted longitudinal wave reflected from a lower extremity of said flaw;

receiving by means of a second transducer located on the same axial side of said flaw as said first transducer and spatially separated from said first transducer said first, second and third returning waves and converting same to first, second, and third signals respectively;

simultaneously displaying by means of a display unit said first, second and third signals;

recognizing said first, second and third signals as comprising a triplet of associated signals if, upon moving said first and second transducers, said first, second and third signals show said triplet's characteristic pattern wherein said first signal's time of arrival is prior to said second signal's time of arrival and said second signal's time of arrival is prior to said third signal's time of arrival, said sequence is substantially independent of the transducers to flaw distance and the first separation comprised of the difference between the time of arrival of said first signal and the time of arrival of said second signal and the second separation comprised of the difference between said time of arrival of said second signal and the time of arrival of said third signal are both substantially independent of said transducers to flaw distance;

measuring said first signal separation;

determining said flaw's depth by using said first signal separation as a proportional indicator of flaw depth.

3. The method of claim 2 further comprising recognizing said first, second and third signals from the background interference by moving said first and second transducers toward and away from said flaw, and observing if said signals' relative amplitudes as shown on said display unit exhibit the characteristic dynamic amplitude pattern of said triplet of associated signals and if the second separation is substantially independent of transducer-to-flaw distance and is dependent on said test specimen's thickness and composition.

4. The method of claim 3 further comprising:

directing said first incident wave from said first transducer into an upper target area located at the upper portion of said region of interest and receiving said first returning wave at said second transducer from said upper target area;

directing said second incident wave from said first transducer into a lower target area located at the lower portion of said region of interest and receiving said second and third returning waves at said second transducer from said lower target area.

5. An ultransonic method for determining the size of a flaw in a region of interest in a test specimen from a single examination surface of said test specimen comprising:

transmitting into said test specimen by means of a first transducer located on a module an incident ultrasonic wave;

moving said module along said examination surface test to insonify through said region of interest with said incident wave;

receiving from said region of interest at a first module position by means of a second transducer located on said module, spatially separated from said first transducer and having a roof angle between it and said first transducer, a first signal comprised of ultrasonic shear waves diffracted by the upper extremity of said flaw as a result of said incident wave;

displaying said first signal on a resolution unit connected to said transducer;

moving said module along said test specimen to move said incident wave further through said region of interest;

receiving from said flaw at a second module position by means of said second transducer a reduced said first signal and a second signal, said second signal comprised of ultrasonic shear waves diffracted from said incident wave by the lower extremity of said flaw;

displaying said first and second signals on said resolution unit;

observing whether the time of arrival separation between of said first signal and said second signal is substantially independent of module to flaw distance;

measuring said separation;

determining the depth of said flaw by using said separation as a proportional indicator of said flaw's depth.

6. The method of claim 1 wherein said first and second transducers are cross-focused through both said upper and lower target areas without being directly above said upper and lower target areas.

7. The method of claim 1 wherein both said transducers are located on a single module, one of said transducers is positioned on said module in front of the other said transducer, both said transducers are bimodal due to their inclination angles with respect to said examination surface, said inclination angles being between 0° to 29° and useful test results may be obtained without moving said module directly over said flaw.

8. The method of claim 7 wherein said inclination angles are in the range of 18° to 27°.

9. The method of claim 8 further comprising calibrating the time base of said display unit in units of said test specimen's through wall distance to cause a linear display of flaw depth at said display unit.

10. The method of claim 9 wherein the delay time between said first signal and a fictitious signal from the flaw base provides a linear indicator of flaw depth.

11. The method of claim 2 wherein said first and second transducers are cross-focused through both said upper and lower target areas, both said transducers are located on a single module, one of said transducers is positioned on said module in front of the other said transducer, both said transducers are bimodal due to their inclination angles with respect to said examination surface, said inclination angles being between 0° and 29° and useful test results may be obtained witout moving said module directly over said flaw.

12. The method of claim 11 further comprising calibrating the time base of said display unit in units of said test specimen's through wall distance to cause a linear display of flaw depth at said display unit.

13. An ultrasonic device for determining the depth of a flaw in a test specimen from a single examination surface comprising:

at least one module capable of being placed upon said test specimen to conduct ultrasonic waves into said test specimen, said module having at least two platforms for locating transducers, a first platform and a second platform, a roof angle between said platforms and greater than zero, an $\alpha^1$ angle between said first platform and the examination surface of said test specimen and an $\alpha^2$ angle between said second platform and said examination surface;

at least two transducers with a first transducer located upon said first platform and a second transducer located upon said second platform;

an ultrasonic test unit connected electrically to said transducers, said ultrasonic test unit comprising a transmitter, a receiver, and a resolution unit;

said $\alpha^2$ angle being inclined to direct a first incident wave from said second transducer to an upper target area within said test specimen and a second incident wave from said second transducer to a lower target area located in said test specimen below said upper target area;

said $\alpha^1$ angle being inclined to permit reception at said first transducer of a first return wave from said upper target area and reception of a second return wave from said lower target area;

said $\alpha^1$ and said $\alpha^2$ angles being sufficiently inclined and said transducers being sufficiently spacially separated to cause said first return wave from interaction of said first incident wave within said upper target area sufficient to produce a useful first signal and said second return wave from interaction of said second incident wave within said lower target area sufficient to produce a useful second signal;

a display unit connected electrically to said ultrasonic test unit capable of displaying said first and second signals to permit measurement of the separation between said first signal's time of arrival and second signal's time of arrival and use of said separation as a proportional indicator of flaw depth.

14. The device of claim 13 wherein said $\alpha^1$ and $\alpha^2$ angles are inclined to cross-focus said transducers through both said upper and lower target areas without said transducers being directly above said upper and lower target areas.

15. The method of claim 13 wherein both said transducers are located on a single module, one of said transducers is positioned on said module in front of the other said transducer, both said transducers are bimodal due to their inclination angles with respect to said examination surface, said inclination angles being between 0° and 29° and useful test results may be obtained without moving said module directly over said flaw.

16. The method of claim 15 wherein said inclination angles are in the range of 18° to 27°.

17. The device of claim 15 wherein said first incident wave is a longitudinal wave, said second incident wave is a shear wave, said first return wave is a longitudinal wave, said second return wave is a shear wave, and said first and second signals are associated signals recognizable through pattern recognition.

18. The device of claim 17 wherein said second transducer additionally transmits a third incident wave comprised of a shear wave, said third incident wave strikes said test specimen's far surface to create a surface wave, said surface wave propagates toward and strikes said flaw's base to create a return longitudinal wave which is received by said first transducer, converted into a third signal and said first, second and third signals are associated signals recognizable by pattern recognition.

19. The device of claim 13 wherein a forward side of said module has a negative slope to permit said module to be moved over the edge of obstructions on said examination surface and closer to said flaw than if said module's forward side were perpendicular to said examination surface.

20. The method of claim 5 wherein said first and second transducers are cross-focused through both said target area without being directly above said target area.

21. The method of claim 5 wherein both of said transducers are located on a single module, one of said transducers is positioned on said module in front of the other said transducer, and useful test results may be obtained without moving said module directly over said flaw.

22. The method of claim 21 further comprising calibrating the time base of said display unit in units of said test specimen's through wall distance to cause a linear display of flaw depth at said display unit.

23. The method of claim 22 wherein the delay time between said first signal and a fictitious signal from the flaw base provides a linear indicator of flaw depth.

24. The method of claim 5 wherein said incident ultrasonic wave is a longitudinal wave and said return waves are shear waves.

25. The method of claim 24 further comprising recognizing said first and second signals by moving said module toward and away from said flaw and observing if said first and second signals' relative amplitudes exhibit the characteristic dynamic amplitude pattern of associated signals to confirm said flaw.

26. The method of claim 5 wherein said incident ultrasonic wave is a shear wave and said return waves are shear waves.

27. The method of claim 24 further comprising recognizing said first and second signals by moving said module toward and away from said flaw and observing if said first and second signals' relative amplitudes exhibit the characteristic dynamic amplitude pattern of associated signals to confirm said flaw.

28. An ultrasonic device for determining the length of a flaw in a test specimen from a single examination surface comprising:
at least one module capable of being placed upon said examination surface of said test specimen to conduct ultrasonic waves into said test specimen, said module having at least two platforms for locating probes, a first platform and a second platform, a roof angle between said platforms greater than zero, an $\alpha^1$ angle between said first platform and said examination surface and an $\alpha^2$ angle between said second platform and said examination surface;
at least two transducers with a first transducer located upon said first platform and a second transducer located upon said second platform;
an ultrasonic test unit connected electrically to said transducers, said ultrasonic test unit comprising a transmitter, a receiver, and a resolution unit;
said $\alpha^2$ angle being sufficient to direct an incident wave at a target area within said test specimen, said incident wave being capable of producing first return waves from a lower extremity of a flaw in said target area and producing second return waves at an upper extremity of said flaw;
said $\alpha^1$ angle being sufficient to permit reception by said first transducer of said first and second return waves from said target area;
said $\alpha^1$ and $\alpha^2$ angles being sufficiently inclined and said transducers being sufficiently spacially separated to cause said first return wave from interaction of said incident wave and said lower flaw extremity sufficient to produce a useful first signal and said second return wave from interaction of said incident wave and said upper flaw extremity sufficient to produce a useful second signal from said transducers and said test unit;
a display unit connected electrically to said ultrasonic test unit capable of displaying said first and second signals to permit measurement of the separation between said first signal's time of arrival and said second signal's time of arrival and use of said separation as a proportional indicator of flaw length.

29. The device of claim 28 wherein said transducers are cross-focused through said target area without being directly above said target area.

30. The method of claim 28 wherein both of said transducers are located on a single module, one of said transducers is positioned on said module in front of the other said transducer, and useful flaw sizing results may be obtained without moving said module directly over said flaw.

31. The device of claim 28 wherein said $\alpha^2$ angle is inclined to cause said incident wave to be a longitudinal wave and said first transducer is positioned and said $\alpha^1$ angle is inclined to permit said first and second return waves to be shear waves and cause said first and second signals to be associated signals recognizable through pattern recognition.

32. The device of claim 28 wherein said $\alpha^2$ angle is inclined to cause said incident wave to be a shear wave and said first transducer is positioned and said $\alpha^1$ angle is inclined to permit said first and second return waves to be shear waves and cause said first and second signals to be associated signals recognizable through pattern recognition.

33. The device of claim 30 wherein a forward side of said module has a negative slope to permit said module to be moved over the edge of obstructions on said examination surface and closer to said flaw than if said module's forward side were perpendicular to said examination surface.

34. A nonplanar multiple transducer array mounted on a common shoe for use with an ultrasonic test unit and display device for detecting and determining the depth of a flaw in a test specimen from a single examination surface of said test specimen comprising:
a least two platforms on said shoe, a first plaform and a second platform, a roof angle between said platforms and greater than zero, a first probe on said first platform and a second probe on said second platform, an $\alpha^1$ angle between said first platform and said examination surface and an $\alpha^2$ angle between said second platform and said examination surface;
at least two transducers with a first transducer located on said first platform and said second transducer located on said second platform, one of said transducers being located in front of the other said transducer;
said $\alpha^2$ angle being sufficient to direct a useful incident transducer longitudinal wave from said second transducer at an upper target area within said test specimen and a useful incident shear wave from sadi second transducer at a lower target area in said test specimen located below said upper target area;
said $\alpha^1$ angle being sufficient to permit reception by said first transducer of a return longitudinal wave created by defraction of said first incident longitudinal wave from an upper flaw extremity in said upper target area and of a return shear wave created by the reflection of said incident shear wave at a lower flaw extremity in said lower target area;

said $\alpha^1$ and $\alpha^2$ angles sufficient to cross-focus said transducers through said upper and lower target areas without said transducers being directly over said upper and lower target areas and being in the range of 18° to 27°.

35. A nonplanar multiple transducer array mounted on a common shoe for use with an ultrasonic test unit and display device for detecting and determining the depth of a flaw in a test specimen from a single examination surface of said test specimen comprising:

at least two platforms on said shoe, a first platform and a second platform, a roof angle between said platforms greater than zero, a first probe on said first platform and a second probe on said second platform, an $\alpha^1$ angle between said first platform and said examination surface and an $\alpha^2$ angle between said second platform and said examination surface, at least two transducers with a first transducer located on said first platform and said second transducer located on said second platform, one of said transducers being located in front of the other said transducer;

said $\alpha^2$ angle being sufficient to direct an incident wave from said second transducer at a target area within said test specimen;

said $\alpha^1$ angle being sufficient to permit recption of a return shear wave at said first transducer created by interaction of said first incident wave at an upper flaw extremity in said target area and reception of a return shear wave at said second transducer created by interaction of said incident wave at a lower flaw extremity in said lower target area, said $\alpha^1$ and $\alpha^2$ angles being sufficient to cross-focus said transducers through said target area without said transducers being directly above said target area.

36. The device of claim 35 wherein said incident wave is a shear wave.

37. The device of claim 35 wherein said incident wave is a longitudinal wave.

38. An ultrasonic test method of detecting a flaw in in a test specimen from a single examination surface comprising:

transmitting into said test specimen by means of a first transducer a first incident wave directed at a target area within said test specimen;

receiving from an upper portion of said target area by means of a second transducer located on the same side of said target area as said first transducer and having a different angular orientation to said examination surface than said second transducer, a first returned wave and converting said first returned wave to a first signal;

transmitting into said test specimen by means of said first transducer a second incident wave directed at a lower target area located below said upper target area;

receiving from a lower portion of said target area by means of said second transducer a second returned wave and converting said second returned wave to a second signal;

displaying by means of a display unit said first and second signals;

recognizing said first and second signals as indicating the presence of a flaw in said target area if, upon moving said first and second transducers, said first signal's sequence of arrival remains prior to said second signal's sequence of arrival and the separation comprised of the difference between said first signal's time of arrival, said second signal's time of arrival is substantially independent of the distance between said target area and said first and second transducers and said first and second signals' relative amplitudes exhibit a characteristic dynamic amplitude pattern of associated signals.

39. The method of claim 38 wherein said second transducer additionally transmits a third incident wave which is converted at said test specimen's far surface to a surface wave, said surface wave propagates to create a third return wave through the medium of a surface wave on said test specimen's far surface which third return wave is received by said first transducer, converted into a third signal and said first, second and third signals are associated signals recognizable by pattern recognition to indicate the presence of a flaw in said target area.

40. An ultrasonic test method of determining a flaw in a test specimen from a single examination surface comprising:

transmitting into said test specimen by means of a first transducer located on a module an incident ultrasonic wave directed at a target area with said test specimen;

receiving from said target area at a second transducer located on said module, spatially separated from said first transducer and having a roof angle between said second transducer and said first transducer, a first signal comprised of ultrasonic shear waves diffracted from a first portion of said target area as a result of said incident wave;

moving said module along said test specimen to move said incident wave further through saids target area;

receiving from target area at a second module position by means of said second transducer a reduced said first signal and a second signal, said second signal comprised of ultrasonic shear waves diffracted from a second portion of said target area as a result of said incident wave;

displaying said first and second signals on said resolution unit;

recognizing said first and second signals as indicating the presence of a flaw in said target area if, upon moving said first and second transducers, said first signal's sequence of arrivalremains prior to said second signal's sequence of arrival and the separation comprised of the difference between said first signal's time of arrival, said second signal's time of arrival is substantially independent of the distance between said target area and said first and second transducers and said first and second signals' relative amplitudes exhibit a characteristic dynamic amplitude pattern of associated signals.

* * * * *